| United States Patent [19] | [11] Patent Number: 4,908,321 |
|---|---|
| Varma | [45] Date of Patent: Mar. 13, 1990 |

[54] RADIO-ACTIVE METHOD FOR DETERMINING TRACE AMOUNTS OF PEROXIDE

[76] Inventor: Shambhu D. Varma, 3126 Paulskirk Dr., Ellicott City, Md. 21043

[21] Appl. No.: 306,526

[22] Filed: Feb. 3, 1989

[51] Int. Cl.$^4$ .................. G01N 23/00; G21H 5/02
[52] U.S. Cl. ........................ 436/57; 436/129; 250/303
[58] Field of Search .............. 424/1.1; 252/645; 250/303; 436/57, 129, 135

[56] References Cited

U.S. PATENT DOCUMENTS 3,832,137  8/1974  Mlinko et al. .............. 250/303 X
3,854,041 12/1974  Waters et al. .................. 250/303

FOREIGN PATENT DOCUMENTS 0035715  9/1974  Japan ............................ 436/129

*Primary Examiner*—John S. Maples
*Attorney, Agent, or Firm*—Louis E. Marn

[57] ABSTRACT

There is disclosed a method of contacting a peroxide containing substance with non-volatile, alpha-keto acid radiolabeled with —$C^{14}$ in the carboxyl group and determining radioactivity evolved $^{14}CO_2$ and thereby calculating the amount of peroxide in the substance.

3 Claims, No Drawings

RADIO-ACTIVE METHOD FOR DETERMINING TRACE AMOUNTS OF PEROXIDE

BACKGROUND OF THE INVENTION (1) Field of the Invention

This invention relates to a method for determining the presence of peroxides in fluids, and more particularly to a method for determining trace quantities of peroxides in fluids by measurement of radioactivity.

(2) Description of the Prior Art

Oxygen is omnipresent and while oxygen is essential for the sustenance of aerobic life, several undesirable phenomena are encountered in life associated with the presence of oxygen. For example, rancidity in food; rusting and crusting of metal, plastic and wooden surfaces; occurrences of certain age dependent diseases, such as retinal degenerations, arthritis, cataracts, cardiac injury as well as a number of other age dependent disabling manifestations. The mechanism through which oxygen brings about such a multitude of effects is complex and not truly understood. An initiating event, in most cases, is the conversion of rather sluggishly reactive oxygen to a reactive species, such as superoxide, hydrogen peroxide, hydroxyl radical, etc., extremely potent oxidants. The formation of superoxide and hydrogen peroxide are considered one of the primary events in oxygen acting as such a potent oxidant.

Superoxide is a very unstable free radical and dismutates rapidly in the presence of moisture to hydrogen peroxide. In the case of nonaqueous substances, such as fatty acids, lipid peroxides can be formed. It is important to know when superoxides and consequently the peroxides are likely to form, and, if so, in what quantities or amounts to anticipate and/or possibly avoid or minimize factors that lead to the adverse oxidative consequences thereof. Thus, it is crucial to have a highly sensitive method for peroxide determination, even if present in only "trace" or very low amounts.

In one of the presently used methods, the peroxide is measured in accordance with the following reaction (1);

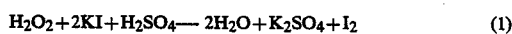

The amount of iodine liberated can be determined by complexing it with starch or by consumption of reagents consuming $I_2$ (iodine); sodium thiosulphate being a common reagent. The method, however, is only applicable for amounts greater than $10^{-6}$ moles/liter of hydrogen peroxide. In addition, the method suffers from the disadvantage that atmospheric oxygen oxidizes iodide into iodine thereby providing a higher value than a true result. Thus, determination of the end point becomes imprecise.

In another method, peroxide is determined by its catalytic decomposition and measuring electrometrically or gasometrically liberated oxygen. Such method is again not sensitive below millimolar levels and suffers from lack of uniformity (in electrometric determination). In addition, in low concentration of the peroxide, catalase is very sluggish in its ability to catalyze the peroxide decomposition.

Certain methods employing fluorescence measurements though applicable at micromolar levels require separation of the already existing fluorophores in the samples. The procedure involved therefore decomposes the peroxide. Furthermore, the exogenous fluorophores used are toxic and carcinogenic.

In most natural situations, particularly in native and experimental biological and nutritional situations, the availability of material for analysis is also very small and the peroxide content in such materials is also very small or present in only trace amounts. Consequently, the determining of the peroxide content in such situations has hitherto been essentially impossible.

OBJECTS OF THE PRESENT INVENTION

An object of the present invention is to provide a novel process for quantitatively analyzing trace amounts of peroxide in a material.

Another object of the present invention is to provide a novel process for quantitative analyzing below micromolar quantities of peroxide in a material.

Yet another object of the present invention is to provide a novel process for quantitative analyzing below micromolar quantities of peroxide in a material unaffected by atmosphere oxygen in ambient native and/or experimental situations.

SUMMARY OF THE INVENTION

These and other objects of the present invention are achieved by allowing contact of a peroxide containing sample with a non-volatile, alpha-keto acid radiolabeled with $-^{14}C$ in the carboxyl group and determining radioactivity of evolved $^{14}CO_2$ and thereby calculating the amount of peroxide in the material.

DETAILED DESCRIPTION OF THE PRESENT INVENTION

The method of the present invention permits the determination of the peroxide content of a material when present even at less than micromolar levels, and down to picomolar ($10^{-12}$) amounts. Broadly, in accordance with the present invention, a suspect substance having peroxide is reacted with a non-volatile, alpha-keto acid radiolabeled with $-^{14}C$ in the alpha position in accordance with the following equation (2):

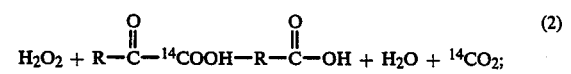

wherein R is an alkyl derivative containing 1 to 6 carbon atoms, such as pyruvic acid, alpha-ketoglutaric acid, keto-malonic acid, oxalacetic acid and 2-keto-L-gluconic acid, etc.

The liberated $^{14}CO_2$ is collected in an alkaline trap and determined by liquid scintillation counting thereby providing a quantification of nano to picomolar levels of peroxide.

Operation of the method of the present invention is described in the following specific examples which are intended to be thereby illustrative and the present invention is intended not to be limited thereto.

EXAMPLE I

The reaction between the peroxide and the ketoacid is carried out in a glass test tube 8.5 cm × 1.8 cm, containing a side arm 2 cm × 0.5 cm. The side arm is situated at a height of about 2.5 cm from the bottom of the tube. The dimensions of the tube and its side arm are variable. Rubber stoppers are used for the side arm as well as the main opening of the tube. The $^{14}CO_2$ trap consists of approximately 6 cm × 0.5 cm filter paper, fluted and packed in a 0.5 ml plastic vial and suspended through a stainless steel loop forced through the main stopper. 200 μl of 1M hyamine hydroxide in methanol is soaked into the filter paper. $H_2O_2$ is diluted in Tyrode to the extent of 1 nanomole/100 μl. 25, 50 and 100 μl. of this solution is then separately introduced into the bottom of the test tubes mentioned hereinabove.

The test tubes are appropriately marked.

The volumes in all the tubes are teen made up to 200 μl by adding appropriate volumes of Tyrode. The blank tube contained 200 μl of Tyrode alone. Additional blanks are prepared by adding 10 μl of catalase (1 mg/2 ml Tyrode) and incubating them for 10 minutes before further processing. 100 μl of a 2.0 mM solution of α-ketoglutaric acid is prepared in Tyrode and pulsed with the radioactive analoque ([I-$^{14}$C]-α-ketoglutaric acid ≈0.01 μCi/100 μl) is then added to the individual tubes. The side arms of the tubes were stoppered before any additions were made. As soon as α-ketoglutarate is added to the tube, it is closed with the $^{14}CO_2$ trap containing stopper. The contents of the tubes are then incubated for 45 to 60 minutes at 37° C.

After this, the tubes are cooled to room temperature for about 5 to 10 minutes. 100 μl of a 20% solution of trichloroacetic acid is then introduced through the side arm using a 1 cc tuberculin syringe and a 27 gauge needle. The withdrawal of the needle is as gentle as possible. While introducing the reactants in the tubes, care is taken to introduce them directly into the bottom, without touching the sides. The usual eppendorf automatic pipetters with long ends are found very useful in this regard. After introduction of the acid, the tubes are reincubated for about an hour at 37° C. to facilitate the transfer of $^{14}CO_2$ from the reaction mixture to the $^{14}CO_2$ trap. The $^{14}CO_2$ traps are then taken out and transferred directly to a vial containing 10 ml of the liquid scintillation mixture. 5 ml of absolute methanol is then added, the vials capped, contents mixed and radioactivity (disintegration) determined in a Beckman Scintillation Counter. Tyrode in the above procedure can be replaced by 1% $NaHCO_3$. Tyrode, however, is a known biological buffer and is useful in many of biological samples.

| Example of Results Experiment No. | | | | |
|---|---|---|---|---|
| Picomoles of $H_2O_2$ in the Reaction Mix | 0 | 25 | 50 | 100 |
| —$C^{14}$ Disintegration per second | 549 | 1319 | 2251 | 4184 |
| —$C^{14}$ Disintegration after-blank Correction | — | 770 | 1702 | 3635 |

The process of the present invention clearly permits picomole analysis of hydrogen peroxide in a sample whether in aqueous or non-aqueous media form and without the use of any carcinogenic material.

The correlation between the radioactive disintegration of the recovered $^{14}CO_2$ and the peroxide content of the reaction mixture is linear. In case of unknown samples, specific activity data can directly be used for calculations, in addition to the determination from standard curve generated as above.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and the equivalents thereof.

What is claimed is:

1. A method for determining the presence of peroxides in less than micromolar amounts contained in a biological and/or non-biological sample, which comprises:
   (a) contacting a suspect sample with a non-volatile acid with the formula,

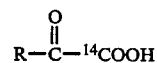

wherein R is an alkyl hydrocarbon or its derivative with from 1 to 6 carbon atoms;
   (b) trapping liberated $^{14}CO_2$;
   (c) determining liberated $^{14}CO_2$ by scintillation counting; and
   (d) evaluating the results of step (c) to determine the peroxide content of said sample.

2. The method for determining the presences of peroxides as defined in claim 1 wherein the acid is selected from the group consisting of pyruvic acid, alpha-ketoglutaric acid, keto-malonic acid, oxalacetic acid and 2-keto-L-gluconic acid.

3. The method for determining the presences of peroxides as defined in claim 2 wherein the acid is α-ketoglutaric acid.

* * * * *